United States Patent
Allegretti et al.

(10) Patent No.: US 7,652,169 B2
(45) Date of Patent: Jan. 26, 2010

(54) (2R)-2-[(4-SULFONYL) AMINOPHENYL] PROPANAMIDES AND PHARMACEUTICAL COMPOSITIONS CONTAINING THEM

(75) Inventors: Marcello Allegretti, L'Aquila (IT); Riccardo Bertini, L'Aquila (IT); Cinzia Bizzarri, L'Aquila (IT); Maria Candida Cesta, L'Aquila (IT); Andrea Aramini, L'Aquila (IT); Alessio Moriconi, L'Aquila (IT)

(73) Assignee: Dompe' Pha. R. Ma S.p.A., L'Aquila (IT)

( * ) Notice: Subject to any disclaimer, the term of this patent is extended or adjusted under 35 U.S.C. 154(b) by 0 days.

(21) Appl. No.: 12/227,519

(22) PCT Filed: May 17, 2007

(86) PCT No.: PCT/EP2007/054806

§ 371 (c)(1),
(2), (4) Date: Nov. 18, 2008

(87) PCT Pub. No.: WO2007/135080

PCT Pub. Date: Nov. 29, 2007

(65) Prior Publication Data

US 2009/0093530 A1     Apr. 9, 2009

(30) Foreign Application Priority Data

May 18, 2006   (EP)   .................................. 06114185

(51) Int. Cl.
 C07C 303/00   (2006.01)
 A01N 41/06    (2006.01)
(52) U.S. Cl. ......................... 564/80; 514/601; 514/602; 514/603
(58) Field of Classification Search .................. 564/80; 514/601, 602, 603
 See application file for complete search history.

(56) References Cited

FOREIGN PATENT DOCUMENTS

WO    WO 01/58852 A2    8/2001
WO    WO 03/043625 A1   5/2003

Primary Examiner—Jafar Parsa
(74) Attorney, Agent, or Firm—Abelman, Frayne & Schwab

(57) ABSTRACT

The present invention relates to novel (2R)-2-phenylpropanamides bearing a 4-sulfonylamino substituent on the 4 position of the phenyl group and to pharmaceutical compositions containing them, which are used as inhibitors of the chemotaxis of polymorphonucleate and mononucleate cells, and which are useful in the treatment of various ELR+CXC chemokine-mediated disorders. In particular, the compounds of the invention are useful in the treatment and control of specific CXCR2 dependent pathologies such as BOS, COPD, angiogenesis and melanoma.

8 Claims, No Drawings

(2R)-2-[(4-SULFONYL) AMINOPHENYL] PROPANAMIDES AND PHARMACEUTICAL COMPOSITIONS CONTAINING THEM

BRIEF DESCRIPTION OF THE INVENTION

The present invention relates to novel (2R)-2-phenylpropanamides bearing a 4-sulfonylamino substituent on the 4 position of the phenyl group and to pharmaceutical compositions containing them, which are used as inhibitors of the chemotaxis of polymorphonucleate and mononucleate cells, and which are useful in the treatment of various ELR$^+$CXC chemokine-mediated disorders. In particular, the compounds of the invention are useful in the treatment and control of specific CXCR2 dependent pathologies such as BOS, COPD, angiogenesis and melanoma.

STATE OF THE ART

Chemokines constitute a large family of chemotactic cytokines that exert their action via an interaction with receptors belonging to the 7TM-GPCRs family. The chemokine system is crucial for the regulation and the control of the basal homeostatic and inflammatory leukocyte movement. The functional consequences of chemokine receptor activation include leukocyte locomotion, degranulation, gene transcription, mitogenic and apoptotic effects. Many cell types, besides the hematopoietic cells, express chemokine receptors; these include endothelia, smooth muscle cells, stromal cells, neurons and epithelial cells. Their activation extends the implications of chemokine receptor activation to other aspects of tissue regulation and homeostasis, such as angiogenesis and the morphogenetic movement during organogenesis in addition to tumor development and metastasis.

Angiogenesis, characterized by the neoformation of blood vessels, is essential for a number of physiological and pathophysiological events, such as embryonic development, wound healing, chronic inflammation and growth of malignant tumors and chemokines influence all these aspects of angiogenesis through different mechanisms. The first strong angiogenic chemokine to be described was CXCL8 (also referred to as IL-8) in 1992 [Koch A. E. et al., Science, 258, 1798, 1992]. From a pathophysiological point of view, the chemokine regulation of angiogenesis seems to be very important in the tumor formation and growth. Two receptors (CXCR1 and CXCR2) for CXCL8 are known; they bind CXCL8 with high affinity. CXCR1 is selective for CXCL8, whereas CXCR2 interacts also with other chemokines as natural ligands. The potential pathogenetic role of CXCL8, CXCR2 mediated, in cutaneous melanoma progression, for instance, is accumulating evidence.

Melanoma specimens and cell lines derived from them have been shown to express several chemokines, including CXCL8 and CXCL1 (also referred to as GRO-α). CXCL8 influences the processes of tumor progression and metastasis because it has been shown to be an autocrine growth factor [Schadendorf D. et al., J. Immunol., 151, 2667, 1993], to induce angiogenesis [Strieter R. M. et al., Am. J. Pathol., 141, 1279, 1992] and to influence migration of melanoma cells [Wang J. M. et al., Biochem. Biophys. Res. Commun., 169, 165, 1990] through the binding and activation of its receptors. Both the receptors are expressed in several cells types (endothelial and melanoma cells) and also have been implicated in the angiogenic response [Addison C. L. et al., J. Immunol., 165, 5269, 2000], but in a different manner. It has been published [Norgauer J. et al. J. Immunol., 156, 1132, 1996] that low expression of CXCR2 can be found on human normal melanocytes, but the receptor is upregulated after treatment with TNF-α, with enhancement of proliferation in response to CXCL8, whereas, in the same experiment, CXCR1 expression is not detectable. CXCL8 as important angiogenic factor is already well assessed, and CXCR2 receptor has been demonstrated to be the putative angiogenic receptor. Only recently the role of the specific receptors CXCR1 and 2 in the melanoma progression has been clarified [Varney M. L. et al., Am. J. Clin. Pathol., 125, 209, 2006]. It has been demonstrated in vitro that, while CXCR1 is expressed ubiquitously in all Clark levels of human malignant melanomas, CXCR2 is expressed predominantly by higher grade melanoma tumors and metastases and that there are meaningful differences in CXCR2 expression levels between thin and thick melanomas, suggesting diverse roles for CXCR2 and CXCR1 also in vivo behaviour. CXCR1 and CXCR2 are implicated in the angiogenic response and in the haptotactic migration/chemotaxis of melanoma cells. Despites similar affinities for CXCL8 and similar receptor numbers, chemotaxis of neutrophils is mediated primarily by CXCR1 [Quan J. M. et al., Biochem. Biophys. Res. Commun., 219, 405, 1996] and the CXCL8 expression by endothelial cells elicits a chemotactic response from melanoma cells through the CXCR1 receptor. The CXCR2 receptor, as above assessed, is considered the putative receptor for mediating ELR$^+$CXC-chemokine-induced angiogenesis, confirming the diverse roles for CXCR1 and CXCR2 in modulating an aggressive malignant phenotype and the association between expression of CXCL8 and CXCR2 but not CXCR1 in melanoma progression and metastasis [Varney M. L. et al., Am. J. Clin. Pathol., 125, 209, 2006].

Inhibition of CXCL8 production and/or activity might be an ideal target, through CXCR2 modulation, for the management of malignant melanoma.

Potential pathogenic role of CXCL8 in pulmonary diseases (lung injury, acute respiratory distress syndrome, asthma, chronic lung inflammation and cystic fibrosis) and, specifically, in the pathogenesis of COPD (chronic obstructive pulmonary disease) through the CXCR2 pathway has been already described [Barnes P J., Cytokine Growth Factor Rev., 14, 511, 2003]. Anti-CXCL8 antibodies have an inhibitory effect on the chemotactic response to COPD sputum [Hill A. T. et al., Am. J. Respir. Crit. Care med., 160, 893, 1999]. COPD is a disease characterized by inflammation on the peripheral airways involving many inflammatory cells and mediators. It is associated with an increased inflammatory cell influx including elevated macrophage numbers in the airways and tissue. Alveolar macrophages develop from monocytes and have the ability to cause the pathological changes associated with COPD. The increased number of macrophages in COPD has been reported as a result of recruitment of monocytes from the circulation. Chemotaxis assays of peripheral blood mononuclear cells from COPD patients show increased chemotactic responses when compared with controls toward GRO-α but not toward MCP-1, CXCL8 or NAP(ENA)-78 [Traves S. L. et al., J. Leuk. Biol., 76, 441, 2004]. This response is not mediated by differences in expression of cellular receptors CXCR1 and CXCR2, but in COPD patients, monocyte expression of CXCR2 is regulated in a different manner: CXCR1 responds to high concentrations of CXCL8 and is responsible for activation of neutrophils and release of superoxide anions and neutrophil elastase, whereas CXCR2 responds to low concentrations of CXC chemokines and is involved in chemotactic responses. Potent SMW molecules inhibitors of CXCR2, such as SB225002, have now been developed as blockers of the chemotactic response of neutrophils to CXCL8 and GRO-α.

This antagonist has a significant inhibitory effect on the chemotactic response to COPD sputum, in which concentrations of GRO-α are elevated [Traves S. L., et al., Thorax, 57, 590, 2002]. CXCR2 antagonists may therefore also reduce monocyte chemotaxis and the accumulation of macrophages in COPD patients. This results highlight the potential of selective CXCR2 vs. CXCR1 SMW antagonists in the therapy for COPD and for the control of lung injury.

More recently, ELR+ CXC chemokines have been hypothesized to have a role also in BOS development. BOS is a fibrotic process resulting in progressive narrowing of bronchiolar lumen and airflow obstruction. BOS typically occurs after adenovirus or *Mycoplasma pneumoniae* infection but it is also associated with chronic rejection of transplanted lungs, especially chronic lung allograft rejection. The cumulative incidence of BOS at 5 years after lung transplantation is between 50% and 80%, and 5-year survival of the graft after BOS onset is only 30%-50% [Douglas, I. S. et al., J. Clin. Invest. 115, 1133, 2005]. BOS is characterized by peribronchiolar leukocytes infiltration that invade and disrupt the submucosa, basement membrane, and airway epithelium. Bronchial tissue damage mediated by leukocyte infiltration and activation is followed by fibroproliferation and granulation tissue formation [Trulock, E. P. Am. J. Respir. Crit Care Med. 155, 789, 1997].

Inhibition of CXCR2 functionality by using anti-CXCR2 Ab inhibited early PMN infiltration in an experimental model of BOS in the mouse [Belperio, J. A., et al., J Clin Invest. 115, 1150, 2005]. Angiogenesis is also considered to crucially contribute to BOS fibroproliferation processes and ELR+ chemokines are supposed to be directly involved in BOS angiogenesis. The angiogenic activity in the BALF of patients with BOS is predominantly due to the presence of ELR+ CXC chemokines. In addition, studies using a murine model of BOS also demonstrated increased vascular remodelling that paralleled ELR+ CXC chemokine expression in tracheal allograft. Taken together, these data support the hypothesis that the pathophysiological role played by ELR+ CXC chemokines in BOS development might be bimodal: in the early phase, ELR+ CXC chemokines affected PMN recruitment (i.e. during the ischemia/reperfusion injury phase) and, in the chronic later phase, they contributed to vascular remodelling and angiogenesis (i.e. during the fibroproliferative phase), strongly suggesting that blockage of ELR+ CXC chemokine activity might be a valid therapeutical strategy for the treatment of this syndrome. The molecules object of the invention, represent, in the treatment and control of specific diseases CXCL8 related, novel therapeutic agents, especially for those pathologies in which it is well assessed a clear physiopathological key role for CXCR2, like BOS, COPD and tumor progression. It is well known that the control of leukocyte movement, activation and differentiation provides the chemokine system with a pivotal role also in the host immune response against invading pathogens. This is supported by the fact that viruses induce or encode chemokines, chemokine receptors or chemokine-binding proteins which, in different ways, manipulate the immune system [Murphy, P M., Nature Immunol., 2, 116, 2001]. It is now clear that the responsiveness to CXCL8 is essential during the earliest phase of the host immune response to infection [McColl S R. et al., J. Immunol., 163, 2829, 1999; Moore T A et al. J. Immunol., 164, 908, 2000], and that CXCR1 is the predominant CXCL8 subtype receptor expressed on human neutrophils. A recent paper [Hess C., et al. Blood, 104, 3463, 2004] described CXCR1 as a system able to define a "rapid-responder" subset of T cells (like CD8+ T cells) that bridges the gap between the innate and acquired immune responses, providing highly cytotoxic antigen-specific effector function early, at site of infection, prior the generation of new effector cells. More, because the levels of CXCR1 on both neutrophils and CD8+ T cells are tightly controlled, the differential responsiveness to CXCR1 agonists/antagonists is an important feature in fine-tuning the immune response. In conclusion it can be hypothesized that in management of chronic diseases in which the main role of CXCR2 is well assessed [i.e. oncologic (melanoma) and pulmonary (COPD, BOS) diseases] the contemporary blockage of CXCR1 receptor (obtained by the most of known CXCL8 modulators) is unnecessary and, in addition, detrimental due to the unnecessary altered immune response consequent to the need of long term treatments.

We have recently described novel classes of "2R-arylpropionylamides" (WO 02/58858) and "2-arylpropionic acids" (WO 03/043625) useful in inhibiting chemotactic activation of PMN leukocytes by the interaction of CXCL8 with CXCR1 and CXCR2. As far as it concerns the class of 2-arylpropionic acids, the biological activity on both the CXCL8 receptors has been claimed and, further, examples of compounds with selective activity on CXCR2 receptor have been described. Concerning the class of amides, no evident selectivity on CXCR1 and CXCR2 subtype receptors had been evidenced inside this class of molecules. Surprisingly, the chemical transformation of a subset of 2-arylpropionic acids in amides, has emphasized the CXCR2 selectivity in compounds otherwise dual CXCR1/2 inhibitors. The marked selectivity and the new physico-chemical characteristics make this subset of amides privileged compounds of this invention, particularly useful for the treatment of specific pathologies CXCR2 dependent in oncology (melanoma) and pulmonary (COPD and BOS) areas.

DISCLOSURE OF THE INVENTION

In the present invention a novel class of (2R)-2-phenylpropanamides bearing a 4-sulfonylamino substituent on the 4 position of the phenyl group and pharmaceutical compositions containing them have been described, which are used as inhibitors of the chemotaxis of polymorphonucleate and mononucleate cells and which are potentially useful in the treatment of various ELR+ CXC chemokine-mediated disorders like acute inflammatory diseases, as COPD, or in ELR+ CXC chemokine-mediated angiogenesis, which can lead to tumorigenesis, like in malignant melanoma. These compounds are characterized by a good water solubility due to the chemical features of the R' ring substituent and independent from the nature of the R residue. Examples of such substituents are alkylsulfonylamino, arylsulfonylamino and heteroarylsulfonylamino groups. Some of the described amides are derived from already described 2-arylpropionic acids which exerted a good specificity toward GROα induced chemotaxis. Surprisingly, the chemical modification of the acids into amides has allowed to obtain novel compounds lacking of activity on CXCR1 receptor and with enhanced activity on CXCR2. The selectivity of the novel described amides toward CXCR2 has been assessed by experiments of inhibition of migration of CXCR1/L1.2 and CXCR2/L1.2 transfectants in response to CXCL8. The data reported in Table I show that the compounds are potent inhibitors of the CXCL1-induced hPMN chemotaxis with an $IC_{50}$ around $10^{-8}M$. By contrast, the same compounds do not significantly inhibit CXCL8 induced hPMN chemotaxis at a concentration $10^{-7}M$. These results are in agreement with the primary role played by CXCR1 in the chemotaxis promotion induced by CXCL8. Coherently, in the selectivity assay, the compounds do not exhibit significant inhibitory activity on the migration of CXCR1/L1.2 transfectants in response to CXCL8 up to $10^{-6}$M.

More, the total lack of activity of cyclooxygenase pathway has been confirmed also for this class of compounds.

On the basis of what has been described above in the introduction, the potential role of this novel class of compounds in the treatment of CXCR2 dependent pathologies, in the oncology area (specifically melanoma) and in the pulmonary area (COPD, BOS), is evident.

DETAILED DESCRIPTION OF THE INVENTION

We have now found a novel class of (2R)-2-phenylpropanamides as inhibitors of the chemotaxis of polymorphonucleate and mononucleate cells. In particular, compounds of the invention thereof are potent inhibitors of CXCL1 induced neutrophils chemotaxis with improved pharmacokinetic and pharmacological activity profile.

The present invention thus provides (2R)-2-phenylpropanamide derivatives of formula (I):

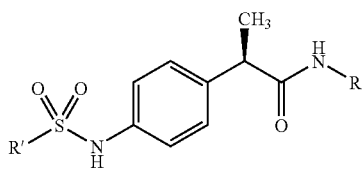

I and pharmaceutically acceptable salts thereof,
wherein
R is selected from
H, OH, $C_1$-$C_5$-alkyl, $C_3$-$C_6$-cycloalkyl, $C_2$-$C_5$-alkenyl, $C_1$-$C_5$-alkoxy and phenyl;
an heteroaryl group selected from substituted and unsubstituted pyrrole, thiophene, furane, indole, imidazole, thiazole, oxazole, pyridine and pirimidine;
a residue of formula —$CH_2$—$CH_2$—O—($CH_2$—$CH_2$O)nR", wherein R" is H or $C_1$-$C_5$-alkyl, n is an integer from 0 to 2;
or R, together with the NH group to which is coupled, is a radical group of primary amides of natural amino acids such as (2S)-2-aminopropanamide, (2S)-2-amino-3-phenylpropanamide, (2S)-2-amino-3-hydroxypropanamide, (2S)-2-amino-3-carboxypropanamide, (2S)-2,6-diaminoexanamide. The NH group mentioned above, as a part of a radical group of primary amides of natural amino acids, represents the amino group of the natural aminoacid.
R' is selected from
linear or branched $C_1$-$C_5$-alkyl, $C_3$-$C_6$-cycloalkyl, $C_2$-$C_5$-alkenyl and trifluoromethyl;
substituted or unsubstituted phenyl;
substituted or unsubstituted benzyl;
an heteroaryl group selected from substituted and unsubstituted pyridine, pirimidine, pyrrole, thiophene, furane, indole, thiazole and oxazole.

The present invention further provides compounds of formula (I) for use as medicaments. In particular, such medicaments are inhibitors of the CXCL1 induced chemotaxis of polymorphonucleate and mononucleate cells.

The compounds of the invention belong to the chemical class of (2R)-2-(4-sulfonylamino phenylpropanamides. Compounds of formula (I) are generically included in the general formulas of the compounds previously described in WO 01/58852, but they share significant advantageous characteristics as compared to the preferred compounds of the above cited inventions.

Surprisingly, this class of compounds shares an enhanced selectivity towards the CXCR2 receptor, respect to the activity showed on the CXCR1 receptor, in the chemotaxis assay, making this class of compounds useful as drugs for treatment of different chronic or acute pathological conditions CXCR2 dependent, especially neoplastic disorders as melanoma. In fact it has been demonstrated that CXCR2 is expressed predominantly by higher grade melanoma tumors and metastases and that there are meaningful differences in CXCR2 expression levels between thin and thick melanomas, suggesting diverse roles for CXCR2 and CXCR1 also in vivo behaviour [Varney M. L. et al., Am. J. Clin. Pathol., 125, 209, 2006]. In addition, CXCR2 antagonists find particularly useful therapeutic applications in the management of important pulmonary diseases like COPD [Hay D. W. P. et al., Current Opinion in Pharmacology, 1, 242, 2001].

Preferred R groups are:
H, $C_1$-$C_5$-alkyl, $C_3$-$C_6$-cycloalkyl, L-2-amino-1-methyl-2-oxoethyl; an heteroaryl group selected from substituted and unsubstituted thiazole, oxazole, pyridine.

Preferred R' groups are:
linear or branched $C_1$-$C_5$-alkyl, $C_3$-$C_6$-cycloalkyl, trifluoromethyl, benzyl; unsubstituted or substituted phenyl with a group selected from halogen, $C_1$-$C_4$-alkyl, $C_1$-$C_4$-alkoxy, trifluoromethyl, thiophene.

Particularly preferred compounds of the invention are:
1-(2R)-2-{4-[(isopropylsulfonyl]amino}phenyl)propanamide;
2-(2R)-2-{4-[(isopropylsulfonyl]amino}phenyl)propanamide sodium salt;
3-(2R)-2-{4-{[(2-chlorophenyl)sulfonyl]amino}phenyl)propanamide;
4-(2R)-2-{4-{[(2,6-dichlorophenyl)sulfonyl]amino}phenyl)propanamide;
5-(2R)-2-{4-[(methylsulfonyl)amino]phenyl}propanamide;
6-(2R)-2-{4-[(phenylsulfonyl)amino]phenyl}propanamide;
7-(2R)-2-{4-{[(4-methylphenyl)sulfonyl]amino}phenyl)propanamide;
8-(2R)-2-{4-{[(4-methoxylphenyl)sulfonyl]amino}phenyl)propanamide;
9-(2R)-2-(4-[(benzylsulfonyl]amino}phenyl)propanamide;
10-(2R)-2-(4-{[(4-chlorophenyl)sulfonyl]amino}phenyl)propanamide;
11-(2R)-2-(4-{[(4-(trifluoromethyl)phenyl]sulfonyl}amino)phenyl]propanamide;
12-(2R)-2-{4-[(thien-2ylsulfonyl)amino]phenyl}propanamide;
13-(2R)-2-{4-[(cyclopentylsulfonyl)amino]phenyl}propanamide;
14-(2R)-2-(4-{[(trifluoromethyl)sulfonyl] amino}phenyl)propanamide;
15-(2R)-2-{4-[(isopropylsulfonyl]amino}phenyl)-N-methylpropanamide;
16-(2R)-N-[(1S)-2-amino-1-methyl-2-oxoethyl]-2-{4-[(isopropylsulfonyl]amino}phenyl)propanamide;
17-(2R)-2-{4-[(isopropylsulfonyl]amino}phenyl)-N-[4-(trifluoromethyl)-1,3-thiazol-2-yl]propanamide;
18-(2R)-2-{4-{[(2-chlorophenyl)sulfonyl]amino}phenyl)-N-[4-(trifluoromethyl)-1,3-thiazol-2-yl]propanamide;
19-(2R)-2-{4-{[(2-chlorophenyl)sulfonyl]amino}phenyl)-N-[2-(2-hydroxyethoxy)ethyl]propanamide;
20-(2R)-2-{4-{[(2-chlorophenyl)sulfonyl]amino}phenyl)-N-cyclopropyl propanamide.

Most preferred compound in the list is compound 1 and the related sodium salt.

The compounds of the invention are potent inhibitors of the human PMNs chemotaxis induced by CXCL1.

The compounds of the invention of formula (I) are generally isolated in the form of their addition salts with both organic and inorganic pharmaceutically acceptable bases.

Examples of these bases are sodium hydroxide, potassium hydroxide, calcium hydroxide, (D,L)-Lysine, L-Lysine, tromethamine.

The compounds of the invention of formula (I) were evaluated in vitro for their ability to inhibit chemotaxis of polymorphonucleate leukocytes (hereinafter referred to as PMNs) and monocytes induced by the fractions of IL-8 and GRO-α. For this purpose, in order to isolate the PMNs from heparinized human blood, taken from healthy adult volunteers, mononucleates were removed by means of sedimentation on dextran (according to the procedure disclosed by W. J. Ming et al., J. Immunol., 138, 1469, 1987) and red blood cells by a hypotonic solution. The cell vitality was calculated by exclusion with Trypan blue, whilst the ratio of the circulating polymorphonucleates was estimated on the cytocentrifugate after staining with Diff Quick.

In the CXCL8 induced chemotaxis assay human recombinant CXCL8 (Pepro Tech) was used as stimulating agents in the chemotaxis experiments: the lyophilized protein was dissolved in a volume of HBSS containing 0.2% bovin serum albumin (BSA) so thus to obtain a stock solution having a concentration of $10^{-5}$ M to be diluted in HBSS to a concentration of $10^{-8}$ M, for the chemotaxis assays.

GRO-α induced chemotaxis inhibition was evaluated in an analogous assay.

In the chemotaxis experiments, the PMNs were incubated with the compounds of the invention of formula (I) for 15' at 37° C. in an atmosphere containing 5% $CO_2$.

During the chemotaxis assay [W. Falket et al., J. Immunol. Methods, 33, 239, 1980] PVP-free filters with a porosity of 5 µm and microchambers suitable for replication were used.

The compounds of the invention in formula (I) were evaluated at a concentration ranging between $10^{-6}$ and $10^{-10}$ M; for this purpose they were added, at the same concentration, both to the lower pores and the upper pores of the microchamber. Evaluation of the ability of the compounds of the invention of formula (I) to inhibit the chemotaxis of human monocytes was carried out according to a disclosed method [Van Damme J. et al., Eur. J. Immunol., 19, 2367, 1989].

The compounds of formula (I) have been tested to assess their selectivity by a migration assay using CXCR1 and CXCR2 transfected L1.2 cells. The assay was performed using 5 µm pore-size Transwell filters and following a described procedure [Imai T. Et al., J. Biol. Chem., 273, 1764, 1998]. L1.2 cells are murine pre-T lymphocytes transfected with a vector (pc-DNA-CXCR1 or CXCR2) containing the gene codifying for the specific protein (CXCR1 or CXCR2). The compounds of formula (I), evaluated ex vivo in the blood in toto according to the procedure disclosed by Patrignani et al., in J. Pharmacol. Exper. Ther., 271, 1705, 1994, were found to be totally ineffective as inhibitors of cyclooxygenase (COX) enzymes.

In most cases, the compounds of formula (I) do not interfere with the production of $PGE_2$ induced in murine macrophages by lipopolysaccharides stimulation (LPS, 1 µg/mL) at a concentration ranging between $10^{-5}$ and $10^{-7}$ M. Inhibition of the production of $PGE_2$ which may be recorded, is mostly at the limit of statistical significance, and more often is below 15-20% of the basal value. The reduced effectiveness in the inhibition of the COXs constitutes an advantage for the therapeutical application of compounds of the invention in as much as the inhibition of prostaglandin synthesis constitutes a stimulus for the macrophage cells to amplify synthesis of TNF-α (induced by LPS or hydrogen peroxide) that is an important mediator of the neutrophilic activation and stimulus for the production of the cytokine Interleukin-8.

Inhibitors of CXCR2 activation find useful applications, as above detailed, particularly in treatment of chronic inflammatory pathologies in which the activation of CXCL8 and GRO-α receptors is supposed to play a crucial pathophysiological role in the development of the disease. Specifically, activation of CXCR2 is supposed to be essential in the mediation of the angiogenic activity of ELR$^+$ CXC chemokines CXCL8-mediated epidermal cell proliferation, angiogenesis and melanoma in animal models [Keane M. P. et al. J. Immunol., 172, 2853, 2004] and in patients with different levels of malignant melanoma [Varney M. L. et al., Am. J. Clin. Pathol., 2006, 125, 209].

In addition, CXCR2 antagonists find particularly useful therapeutic applications in the management of important pulmonary diseases like chronic obstructive pulmonary disease (COPD) (D. W P Hay and H. M. Sarau., Current Opinion in Pharmacology 2001, 1:242-247) and bronchiolitis obliterans syndrome (BOS) [Trulock, E. P. Am. J. Respir. Crit Care Med. 155, 789, 1997].

It is therefore a further object of the present invention to provide compounds for use in the treatment of angiogenesis, melanoma, chronic obstructive pulmonary disease (COPD) and bronchiolitis obliterans syndrome (BOS), as well as the use of such compounds in the manufacture of a medicament for the treatment of diseases as described above.

Pharmaceutical compositions comprising a compound of the invention and a suitable carrier thereof, are also within the scope of the present invention.

The compounds of the invention, together with a conventionally employed adjuvant, carrier, diluent or excipient may, in fact, be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the compounds of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined on the basis of relevant circumstances including the condition to be treated, the chosen route of administration, the actual compound administered, the age, weight, and response of the individual patient, the severity of the patient's symptoms, and the like.

The pharmaceutical compositions of the invention can be administered by a variety of routes including oral, rectal, transdermaldermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Liquid forms, including the injectable compositions described herebelow, are always stored in the absence of light, so as to avoid any catalytic effect of light, such as hydroperoxide or peroxide formation. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the acid derivative of formula (I) in such compositions is typically a minor component, frequently ranging between 0.05 to 10% by weight with the remainder being the injectable carrier and the like. The mean daily dosage will depend upon various factors, such as the seriousness of the disease and the conditions of the patient (age, sex and weight). The dose will generally vary from 1 mg or a few mg up to 1500 mg of the compounds of formula (I) per day, optionally divided into multiple administrations. Higher dosages may be administered also thanks to the low toxicity of the compounds of the invention over long periods of time.

The above described components for orally administered or injectable compositions are merely representative. Further materials as well as processing techniques and the like are set out in Part 8 of "Remington's Pharmaceutical Sciences Handbook", 18$^{th}$ Edition, 1990, Mack Publishing Company, Easton, Pa., which is incorporated herein by reference.

The compounds of the invention can also be administered in sustained release forms or from sustained release drug delivery systems. A description of representative sustained release materials can also be found in the incorporated materials in the Remington's Handbook as above.

The present invention shall be illustrated by means of the following examples which are not construed to be viewed as limiting the scope of the invention.

EXAMPLES

The alkyl and arylsulfonyl chlorides used as reagents in the synthesis of compounds of formula (I) are known products, generally commercially available or they can be prepared according to methods described in the literature.

(2R)-2-(4-Aminophenyl)propanamide (2R)-2-(4-Nitrophenyl)propanoic acid (6 g, 30.6 mmol) was dissolved in dry $CH_2Cl_2$ (80 mL) and 1,1-carbonyldiimidazole (5.58 g, 34.41 mmol) was added and the resulting solution stirred at room temperature for 2 h. Gaseous ammonia was then bubbled into the solution until complete disappearance of the interm diate as checked by IR analysis (8 h). A saturated solution of $NH_4Cl$ (20 mL) was added to the organic solution and the two phases were debated and separated. The organic one was washed again with water (2×25 mL), dried over $Na_2SO_4$, filtered and evaporated under vacuum to give (2R)-2-(4-nitrophenyl)propanamide as white solid (5.1 g, 26.15 mmol).

(2R)-2-(4-Nitrophenyl)propanamide (4.9 g, 25.2 mmol) was dissolved in a mixture of THF (30 mL) and $CH_3OH$ (30 mL) and the resulting solution cooled at T=0-5° C. Ammonium formate (8 g, 126.mmol) was added and, then, also 10% Pd/C (1.6 g) was added portionwise and carefully. The resulting mixture was left stirring at room temperature overnight, until complete disappearance of the starting material (by TLC). After under vacuum filtration over a celite cake, and solvents evaporation at reduced pressure, the pure (2R)-2-(4-aminophenyl)propanamide was isolated as white powder (4 g, 24.24 mmol). Yield 96.2%. m.p. 110-112° C.; $[\alpha]_D^{25}$ (c=0.6, $CH_3OH$): −1.9°; $^1$H-NMR ($CDCl_3$) δ 7.10 (d, 2H, J=7 Hz), 6.65 (d, 2H, J=7 Hz), 5.35 ((bs, 2H, $CONH_2$), 3.52 (m, 1H), 1.50 (d, 3H, J=7 Hz).

(2R)-2-{4-[(Isopropylsulfonyl]amino}phenyl)propanamide (1)

(2R)-2-4-Aminophenyl)propanamide (0.5 g, 3.05 mmol) was dissolved in pyridine (2 mL) and 2-propanesulfonyl chloride (0.53 mL, 3.66 mmol) was added. The resulting solution was refluxed for 4 h and left overnight at room temperature. After the complete disappearance of the starting amide, the solution was diluted with $Et_2O$ (10 mL) and the organic layer washed with 1N HCl (2×5 mL), with $H_2O$ (2×5 mL), dried over $Na_2SO_4$, filtered and evaporated under vacuum to give (2R)-2-{(4-[(isopropylsulfonyl)amino]phenyl}propanamide as pale yellow solid (667 mg, 2.47 mmol). Yield 81%. mp 125-127° C.; $[\alpha]_D^{25}$ (c=0.3, $CH_3OH$): −12.7°; $^1$H-NMR (DMSO-$d_6$) δ 9.65 (bs, 1H, $SO_2NH$), 7.40 (bs, 1H, $CONH_2$), 7.25 (d, 2H, J=7 Hz), 7.12 (d, 2H, J=7 Hz), 6.80 (bs, 1H, $CONH_2$), 3.52 (q, 1H, J=7 Hz), 3.15 (m, 1H), 1.22 (d, 3H, J=7 Hz), 1.18 (d, 6H, J=7 Hz).

Following the procedure above described and starting from the appropriate sulfonyl chlorides, the following amides were prepared:

(2R)-2-{4-{[(2-chlorophenyl)sulfonyl]amino}phenyl) propanamide (2); waxy solid; $[\alpha]_D^{25}$ (c=0.5, $CH_3OH$): −8.3°; $^1$H-NMR ($CDCl_3$) δ 8.10 (d, 1H, J=7 Hz), 7.52-7.45 (m, 2H+NH), 7.32-7.27 (m, 1H), 7.13 (d, 2H, J=7 Hz), 7.05 (d, 2H, J=7 Hz), 5.55 (bs, 1H, $CONH_2$), 5.28 (bs, 1H, $CONH_2$), 3.48 (q, 1H, J=7 Hz), 1.42 (d, 3H, J=7 Hz).

(2R)-2-{4-{[(2,6-dichlorophenyl)sulfonyl] amino}phenyl)propanamide (3); waxy solid; $[\alpha]_D^{25}$ (c=0.5, $CH_3OH$): −10°; $^1$H-NMR ($CDCl_3$) δ 7.52 (bs, 1H, NH), 7.35-7.20 (m, 3H), 7.13 (d, 2H, J=7 Hz), 7.05 (d, 2H, J=7 Hz), 5.55 (bs, 1H, $CONH_2$), 5.28 (bs, 1H, $CONH_2$), 3.48 (q, 1H, J=7 Hz), 1.42 (d, 3H, J=7 Hz).

(2R)-2-{4-[(methylsulfonyl)amino]phenyl}propanamide (4); waxy solid; $[\alpha]_D^{25}$ (c=0.5, $CH_3OH$): −12.5°; $^1$H-NMR (DMSO-$d_6$) δ 9.65 (bs, 1H, NH), 7.40 (bs, 1H, $CONH_2$), 7.25 (d, 2H, J=7 Hz), 7.12 (d, 2H, J=7 Hz), 6.80 (bs, 1H, $CONH_2$), 3.64 (s, 3H), 3.52 (q, 1H, J=7 Hz), 1.22 (d, 3H, J=7 Hz).

(2R)-2-{4-[(phenylsulfonyl)amino]phenyl}propanamide (5); white powder; mp 152-153° C.; $[\alpha]_D^{25}$ (c=0.5, $CH_3OH$): −13.5°; $^1$H-NMR (DMSO-$d_6$) δ 7.92 (m, 2H), 7.74-7.62 (m, 3H+NH), 7.40 (bs, 1H, CONH$_2$), 7.30 (d, 2H, J=7 Hz), 7.15 (d, 2H, J=7 Hz), 6.88 (bs, 1H, CONH$_2$), 3.60 (q, 1H, J=7 Hz), 1.40 (d, 3H, J=7 Hz).

(2R)-2-{4-{[(4-methylphenyl)sulfonyl]amino}phenyl) propanamide (6); white powder; mp 138-140° C.; $[\alpha]_D^{25}$ (c=0.2, CH$_3$OH): −7.1°; $^1$H-NMR (CDCl$_3$) δ 7.65 (d, 2H, J=7 Hz), 7.28-7.15 (m, 4H), 7.05 (d, 2H, J=7 Hz), 6.45 (bs, 1H, NH), 5.25 (bs, 1H, CONH$_2$), 3.52 (q, 1H, J=7 Hz), 2.38 (s, 3H), 1.47 (d, 3H, J=7 Hz).

(2R)-2-{4-{[(4-methoxylphenyl)sulfonyl]amino}phenyl) propanamide (7); white powder; mp 118-120° C.; $[\alpha]_D^{25}$ (c=0.2, CH$_3$OH): −3.6°; $^1$H-NMR (CDCl$_3$) δ 7.70 (d, 2H, J=7 Hz), 7.22 (d, 2H, J=7 Hz), 7.05 (d, 2H, J=7 Hz), 6.90 (d, 2H, J=7 Hz), 6.52 (bs, 1H, NH), 5.25 (bs, 2H, CONH$_2$), 3.85 (s, 3H), 3.55 (q, 1H, J=7 Hz), 1.45 (d, 3H, J=7 Hz).

(2R)-2-(4-{[benzylsulfonyl]amino}phenyl)propanamide (8); white powder; mp 68-70° C.; $[\alpha]_D^{25}$ (c=0.2, CH$_3$OH): −2.5°; $^{1H\text{-}NMR\,(CDCl}_3$) δ 7.40-7.35 (m, 3H), 7.30-7.25 (m, 4H), 7.15 (d, 2H, J=7 Hz), 6.21 (bs, 1H, NH), 5.31 (bs, 2H, CONH$_2$), 4.35 (s, 2H), 3.58 (q, 1H, J=7 Hz), 1.57 (d, 3H, J=7 Hz).

(2R)-2-(4-{[(4-chlorophenyl)sulfonyl]amino}phenyl) propanamide (9); white powder; mp 150-153° C.; $[\alpha]_D^{25}$ (c=0.2, CH$_3$OH): −3.6°; $^1$H-NMR (CDCl$_3$) δ 7.75 (d, 2H, J=7 Hz), 7.45 (d, 2H, J=7 Hz), 7.25 (d, 2H, J=7 Hz), 7.05 (d, 2H, J=7 Hz), 6.68 (bs, 1H, NH), 5.28 (bs, 2H, CONH$_2$), 3.55 (q, 1H, J=7 Hz), 1.50 (d, 3H, J=7 Hz).

(2R)-2-(4-{[(4-(trifluoromethyl)phenyl]sulfonyl}amino) phenyl]propanamide (10); white powder; mp 178-180° C.; $[\alpha]_D^{25}$ (c=0.2, CH$_3$OH): −2.5°; $^1$H-NMR (CDCl$_3$) δ 9.20 (bs, 1H, NH), 7.90 (d, 2H, J=7 Hz), 7.68 (d, 2H, J=7 Hz), 7.15 (d, 2H, J=7 Hz), 7.05 (d, 2H, J=7 Hz), 5.45-5.30 (bs, 2H, CONH$_2$), 3.48 (q, 1H, J=7 Hz), 1.45 (d, 3H, J=7 Hz).

(2R)-2-{4-[(thien-2ylsulfonyl)amino] phenyl}propanamide (11); white powder; mp 58-60° C.; $[\alpha]_D^{25}$ (c=0.2, CH$_3$OH): −3.5°; $^1$H-NMR (CDCl$_3$) δ 7.58 (d, 1H, J=2 Hz), 7.52 (d, 1H, J=2 Hz), 7.25 (d, 2H, J=7 Hz), 7.10 (d, 2H, J=7 Hz), 7.05 (d, 1H, J=2 Hz), 6.75 (bs, 1H, NH), 5.35 (bs, 2H, CONH$_2$), 3.58 (q, 1H, J=7 Hz), 1.48 (d, 3H, J=7 Hz).

(2R)-2-{4-[(cyclopentylsulfonyl)amino] phenyl}propanamide (12); waxy solid; $[\alpha]_D^{25}$ (c=0.5, CH$_3$OH): −10.2°; $^1$H-NMR (DMSO-d$_6$) δ 7.75 (bs, 1H, NH), 7.40 (bs, 1H, CONH$_2$), 7.30 (d, 2H, J=7 Hz), 7.15 (d, 2H, J=7 Hz), 6.88 (bs, 1H, CONH$_2$), 3.60 (q, 1H, J=7 Hz), 3.34 (m, 1H), 2.08-1.97 (m, 2H), 1.85-1.75 (m, 2H), 1.60-1.50 (m, 4H), 1.40 (d, 3H, J=7 Hz).

(2R)-2-(4-{[(trifluoromethyl)sulfonyl]amino}phenyl) propanamide (13); waxy solid; $[\alpha]_D^{25}$ (c=0.5, CH$_3$OH): −24.5°; $^1$H-NMR (DMSO-d$_6$) δ 9.60 (bs, 1H, NH), 7.65 (d, 2H, J=7 Hz), 7.40 (bs, 1H, CONH$_2$), 7.12 (d, 2H, J=7 Hz), 6.85 (bs, 1H, CONH$_2$), 3.52 (q, 1H, J=7 Hz), 1.40 (d, 3H, J=7 Hz).

(2R)-2-{4-[(isopropylsulfonyl]amino}phenyl)-N-methylpropanamide (14)

(2R)-2-{[4-(isopropylsulfonylamino)phenyl]}propanoic, prepared as described in WO 03/042625, (0.65 g, 2.4 mmol) was dissolved in CH$_2$Cl$_2$ (8 mL); N-(3-dimethylaminopropyl)-N'-ethylcarbodiimide hydrochloride (WSC) (0.46 g, 2.4 mmol) and 1-hydroxybenzotriazole hydrate (HOBT) (0.324 g, 2.4 mmol) were added and the resulting mixture was left stirring at room temperature for 30'. Then a mixture of methylamine hydrochloride (0.155 g, 2.43 mmol) and triethylamine (0.33 mL, 2.4 mmol) in CH$_2$Cl$_2$ (2 mL) was added by dripping and the resulting mixture was left stirring at room temperature overnight. The mixture was diluted with CH$_2$Cl$_2$ (10 mL) and the organic layer washed with 1N HCl (2×10 mL) and with H$_2$O (2×10 mL), dried over Na$_2$SO$_4$, filtered and evaporated under vacuum to give (2R)-2-{4-[(isopropylsulfonyl]amino}phenyl)-N-methylpropanamide as waxy solid (0.63 g, 2.23 mmol). Yield 93%. $[\alpha]_D^{25}$ (c=1, CH$_3$CH$_2$OH): −20.5°; $^1$H-NMR (CDCl$_3$) δ 9.65 (bs, 1H, SO$_2$NH), 7.25 (d, 2H, J=7 Hz), 7.12 (d, 2H, J=7 Hz), 5.30 (bs, 1H, NH), 3.52 (q, 1H, J=7 Hz), 3.15 (m, 1H), 2.78 (d, 3H, J=3 Hz), 1.22 (d, 3H, J=7 Hz), 1.18 (d, 6H, J=7 Hz).

Following the procedure above described and starting from the appropriate commercial amines hydrochlorides and propanoic acids of formula (II)

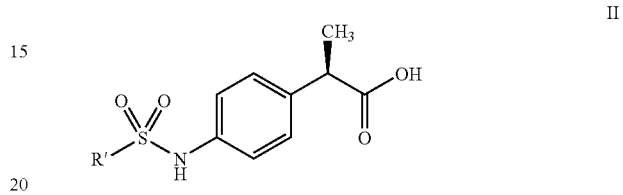

II wherein R' is as defined above, the following amides were prepared:

(2R)-N-[(1S)-2-amino-1-methyl-2-oxoethyl]-2-{4-[(isopropylsulfonyl]amino}phenyl)propanamide (15); white powder; mp 132-135° C.; $[\alpha]_D^{25}$ (c=1, CH$_3$OH): −22.5°; $^1$H-NMR (DMSO-d$_6$) δ 9.65 (bs, 1H, SO$_2$NH), 8.35 (bs, 1H, NH), 7.70 (d, 2H, J=7 Hz), 7.62 (d, 2H, J=7 Hz), 7.50-7.35 (bs, 1H, CONH$_2$), 7.15-7.05 (bs, 1H, CONH$_2$), 4.45-4.32 (m, 1H), 4.05 (q, 1H, J=7 Hz), 3.15 (m, 1H), 1.55 (d, 3H, J=7 Hz), 1.35 (d, 3H, J=7 Hz), 1.18 (d, 6H, J=7 Hz).

(2R)-2-{4-[(isopropylsulfonyl]amino}phenyl)-N-[4-(trifluoromethyl)-1,3-thiazol-2-yl]propanamide (16); glassy solid; $[\alpha]_D^{25}$ (c=0.5, CH$_3$OH): −8.4°; $^1$H-NMR (CDCl$_3$) δ 9.65 (bs, 1H, SO$_2$NH), 8.75 (bs, 1H, NH), 7.45 (d, 2H, J=7 Hz), 7.30 (d, 2H, J=7 Hz), 7.25 (s, 1H), 3.82 (q, 1H, J=7 Hz), 3.15 (m, 1H), 1.24 (d, 3H, J=7 Hz), 1.15 (d, 6H, J=7 Hz).

(2R)-2-{4-{[(2-chlorophenyl)sulfonyl]amino}phenyl)-N-[4-(trifluoromethyl)-1,3-thiazol-2-yl]propanamide (17); waxy solid; $[\alpha]_D^{25}$ (c=0.5, CH$_3$OH): −5.5°; $^1$H-NMR (CDCl$_3$) δ 9.50 (bs, 1H, SO$_2$NH), 8.72 (bs, 1H, NH), 8.10 (d, 1H, J=7 Hz), 7.50-7.48 (m, 2H), 7.32-7.27 (m, 1H), 7.20 (s, 1H), 7.13 (d, 2H, J=7 Hz), 7.05 (d, 2H, J=7 Hz), 3.48 (q, 1H, J=7 Hz), 1.42 (d, 3H, J=7 Hz).

(2R)-2-{4-{[(2-chlorophenyl)sulfonyl]amino}phenyl)-N-[2-(2-hydroxyethoxy)ethyl]propanamide (18); colourless oil; $[\alpha]_D^{25}$ (c=0.5, CH$_3$OH): −4.5°; $^1$H-NMR (CDCl$_3$) δ 9.50 (bs, 1H, SO$_2$NH), 8.10 (d, 1H, J=7 Hz), 7.50-7.48 (m, 2H), 7.32-7.27 (m, 1H), 7.15 (d, 2H, J=7 Hz), 7.08 (d, 2H, J=7 Hz), 6.10 (bs, 1H, NH), 3.70-3.60 (m, 3H), 3.55-3.40 (m, 6H), 2.05 (bs, 1H, OH), 1.52 (d, 3H, J=7 Hz).

(2R)-2-{4-{[(2-chlorophenyl)sulfonyl]amino}phenyl)-N-cyclopropylpropanamide (19); colourless oil; $[\alpha]_D^{25}$ (c=0.5, CH$_3$OH): −11.5°; $^1$H-NMR (CDCl$_3$) δ 9.50 (bs, 1H, SO$_2$NH), 8.10 (d, 1H, J=7 Hz), 7.50-7.48 (m, 2H), 7.32-7.27 (m, 1H), 7.15 (d, 2H, J=7 Hz), 7.08 (d, 2H, J=7 Hz), 5.45 (bs, 1H, NH), 3.50 (q, 1H, J=7 Hz), 2.75-2.62 (m, 1H), 1.52 (d, 3H, J=7 Hz), 0.8 (m, 2H), 0.42 (m, 2H).

(2R)-2-{4-[(Isopropylsulfonyl]amino}phenyl)propanamide sodium salt (2R)-2-{(4-[(Isopropylsulfonyl)amino]phenyl propanamide (1) (500 mg, 1.85 mmol) was dissolved in CH$_3$OH (15 mL). NORMEX 1N NaOH (1.85 mL, 1.85 mmol) was added by dripping and the resulting solution was left stirring at room temperature for 2 h. After solvent evaporation, water (3 mL) was added and the clear solution was frozen and then lyophilized to give (2R)-2-{4-[(isopropylsulfonyl]amino}phenyl)propanamide sodium salt (541 mg, 1.85 mmol) as pale yellow powder. Quantitative yield. $[\alpha]_D^{25}$ (c=0.4, CH$_3$OH): −11.75°; $^1$H-NMR (D$_2$O) δ 7.32 (d, 2H, J=7 Hz), 7.15 (d, 2H, J=7 Hz), 3.82 (q, 1H, J=7 Hz), 3.35 (m, 1H), 1.54 (d, 3H, J=7 Hz), 1.35 (d, 6H, J=7 Hz).

The sodium salts of compounds 2-19 have been prepared following the same procedure above described.

Table I reports biological activity of exemplary compounds of the present invention.

TABLE I

| Name | Structure | CXCL1 (% inhibition at $10^{-8}$ M) | CXCL8 (% inhibition at $10^{-7}$ M) |
|---|---|---|---|
| (2R)-2-{4-[(isopropylsulfonyl]amino}phenyl) propanamide (1) | 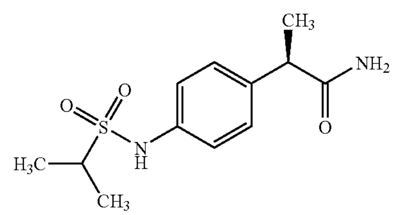 | 67 ± 7 | 7 ± 18 |
| (2R)-2-{4-{[(2-chlorophenyl)sulfonyl]amino}phenyl) propanamide (2) | 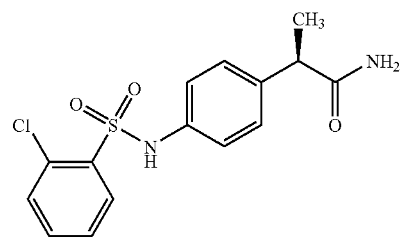 | 41 ± 7 | 19 ± 5 |
| (2R)-2-{4-{[(2,6-dichlorophenyl)sulfonyl]amino}phenyl) propanamide (3) | 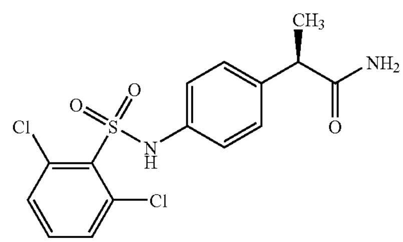 | 39 ± 10 | 14 ± 5 |
| (2R)-2-{4-[(methylsulfonyl)amino]phenyl} propanamide (4) | 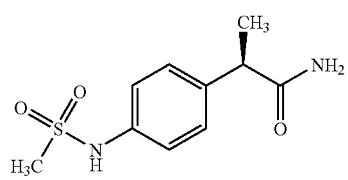 | 75 ± 7 | 10 ± 7 |
| (2R)-2-{4-[(phenylsulfonyl)amino]phenyl} propanamide (5) | 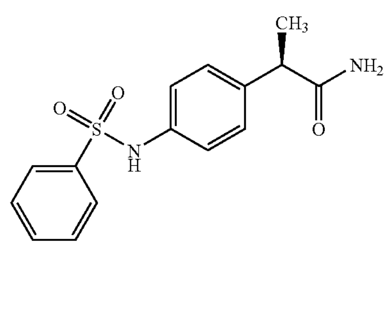 | 44 ± 9 | 15 ± 10 |

TABLE I-continued

| Name | Structure | CXCL1 (% inhibition at $10^{-8}$ M) | CXCL8 (% inhibition at $10^{-7}$ M) |
| --- | --- | --- | --- |
| (2R)-2-{4-{[(4-methylphenyl)sulfonyl]amino}phenyl)propanamide (6) | 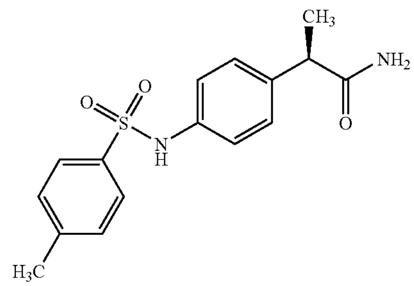 | 65 ± 4 | 12 ± 10 |
| (2R)-2-{4-{[(4-methoxyphenyl)sulfonyl]amino}phenyl)propanamide (7) | | 71 ± 11 | 9 ± 7 |
| (2R)-2-(4-[(benzylsulfonyl]amino}phenyl)propanamide (8) | 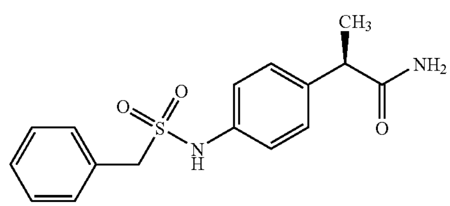 | 58 ± 6 | 14 ± 9 |
| (2R)-2-(4-{[(4-chlorophenyl)sulfonyl]amino}phenyl)propanamide (9) | 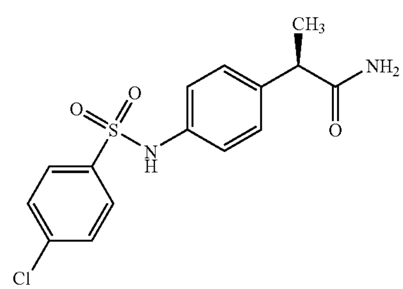 | 53 ± 12 | 20 ± 4 |
| (2R)-2-(4-{[(4-(trifluoromethyl)phenyl]sulfonyl}amino)phenyl]propanamide (10) | 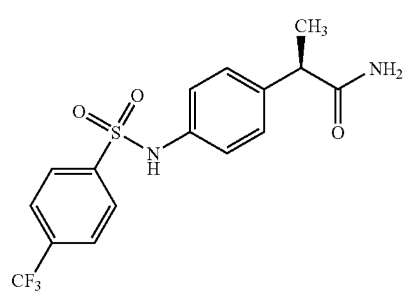 | 69 ± 5 | 15 ± 7 |

TABLE I-continued

| Name | Structure | CXCL1 (% inhibition at $10^{-8}$ M) | CXCL8 (% inhibition at $10^{-7}$ M) |
|---|---|---|---|
| (2R)-2-{4-[(thien-2ylsulfonyl)amino]phenyl}propanamide (11) | 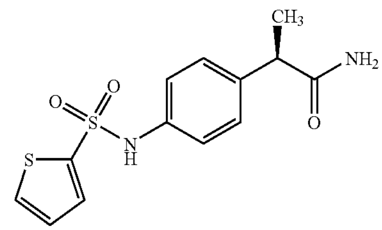 | 50 ± 2 | 17 ± 4 |
| (2R)-2-{4-[(cyclopentylsulfonyl)amino]phenyl}propanamide (12) | 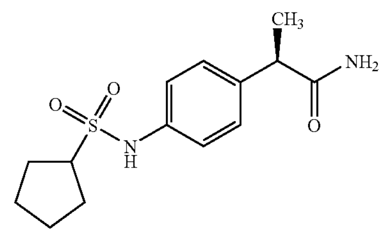 | 67 ± 7 | 21 ± 10 |
| (2R)-2-(4-{[(trifluoromethyl)sulfonyl]amino}phenyl)propanamide (13) | 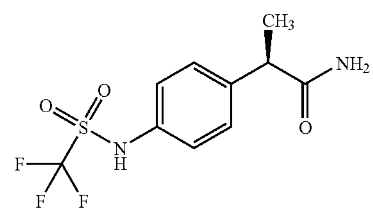 | 75 ± 11 | 24 ± 7 |
| (2R)-2-{4-[(isopropylsulfonyl]amino}phenyl)-N-methylpropanamide (14) | 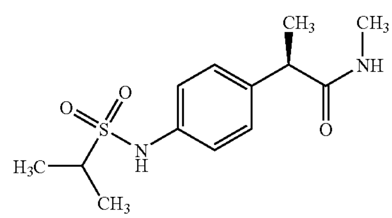 | 64 ± 8 | 8 ± 9 |
| (2R)-N-[(1S)-2-amino-1-methyl-2-oxoethyl]-2-{4-[(isopropylsulfonyl]amino}phenyl)propanamide (15) | 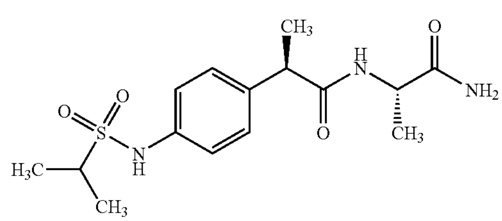 | 58 ± 2 | 10 ± 8 |
| (2R)-2-{4-[(isopropylsulfonyl]amino}phenyl)-N-[4-(trifluoromethyl)-1,3-thiazol-2-yl]propanamide (16) | 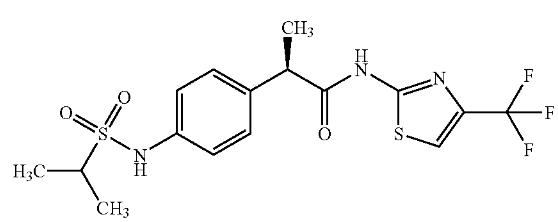 | 49 ± 10 | 11 ± 7 |

TABLE I-continued

| Name | Structure | CXCL1 (% inhibition at $10^{-8}$ M) | CXCL8 (% inhibition at $10^{-7}$ M) |
| --- | --- | --- | --- |
| (2R)-2-{4-{[(2-chlorophenyl)sulfonyl]amino}phenyl)-N-[4-(trifluoromethyl)-1,3-thiazol-2-yl]propanamide (17) | 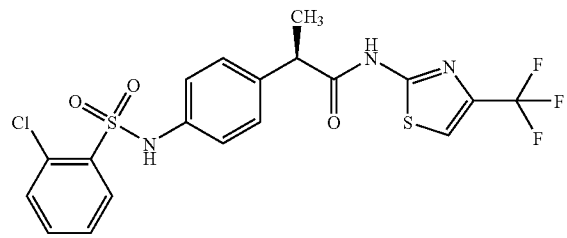 | 40 ± 12 | 14 ± 11 |
| (2R)-2-{4-{[(2-chlorophenyl)sulfonyl]amino}phenyl)-N-[2-(2-hydroxyethoxy)ethyl]propanamide (18) | 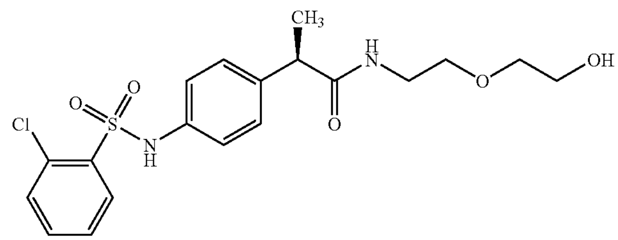 | 59 ± 5 | 6 ± 7 |
| (2R)-2-{4-{[(2-chlorophenyl)sulfonyl]amino}phenyl)-N-cyclopropylpropanamide (19) | 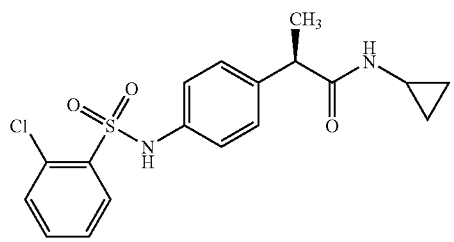 | 60 ± 8 | 19 ± 4 |

The invention claimed is:

1. (2R)-2-phenylpropanamide derivatives of formula (I):

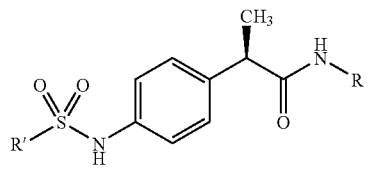

I and pharmaceutically acceptable salts thereof, wherein

R is selected from
H, OH, $C_1$-$C_5$-alkyl, $C_3$-$C_6$-cycloalkyl, $C_2$-$C_5$-alkenyl, $C_1$-$C_5$-alkoxy and phenyl;
an heteroaryl group selected from substituted and unsubstituted pyrrole, thiophene, furane, indole, imidazole, thiazole, oxazole, pyridine and pirimidine;
a residue of formula —$CH_2$—$CH_2$—O—($CH_2$—$CH_2$O)nR", wherein R" is H or $C_1$-$C_5$-alkyl, n is an integer from 0 to 2;
or R, together with the NH group to which is coupled, is a radical group of primary amides of natural amino acids such as (2S)-2-aminopropanamide, (2S)-2-amino-3-phenylpropanamide, (2S)-2-amino-3-hydroxypropanamide, (2S)-2-amino-3-carboxypropanamide, (2S)-2,6-diaminoexanamide;

R' is selected from
linear or branched $C_1$-$C_5$-alkyl, $C_3$-$C_6$-cycloalkyl, $C_2$-$C_5$-alkenyl and trifluoromethyl;
substituted or unsubstituted phenyl;
substituted or unsubstituted benzyl;
an heteroaryl group selected from substituted and unsubstituted pyridine, pirimidine, pyrrole, thiophene, furane, indole, thiazole and oxazole.

2. Compounds according to claim 1 wherein
R is selected from
H, $C_1$-$C_5$-alkyl, $C_3$-$C_6$-cycloalkyl, L-2-amino-1-methyl-2-oxoethyl;
an heteroaryl group selected from substituted and unsubstituted thiazole, oxazole, pyridine;
R' is selected from
linear or branched $C_1$-$C_5$-alkyl, $C_3$-$C_6$-cycloalkyl, trifluoromethyl, benzyl;
unsubstituted or substituted phenyl with a group selected from halogen, $C_1$-$C_4$-alkyl, $C_1$-$C_4$-alkoxy, trifluoromethyl, thiophene.

3. Compounds according to claim 1 or 2 selected from:
(2R)-2-{4-[(isopropylsulfonyl]amino} phenyl)propanamide;
(2R)-2-{4-[(isopropylsulfonyl]amino } phenyl)propanamide sodium salt;
(2R)-2-{4-{[(2-chlorophenyl)sulfonyl]amino } phenyl) propanamide;
(2R)-2-{4-{[(2,6-dichlorophenyl)sulfonyl]amino } phenyl) propanamide;

(2R)-2-{4-[(methylsulfonyl)amino]phenyl} propanamide;
(2R)-2-{4-[(phenylsulfonyl)amino]phenyl}propanamide;
(2R)-2-{4-{[(4-methylphenyl)sulfonyl]amino} phenyl) propanamide;
(2R)-2-{4-{[(4-methoxylphenyl)sulfonyl]amino} phenyl) propanamide;
(2R)-2-(4-[(benzylsulfonyl]amino} phenyl)propanamide;
(2R)-2-(4-{[(4-chlorophenyl)sulfonyl]amino} phenyl) propanamide;
(2R)-2-(4-{[(4-(trifluoromethyl)phenyl]sulfonyl}amino) phenyl]propanamide;
(2R)-2-{4-[(thien-2ylsulfonyl)amino]phenyl} propanamide;
(2R)-2-{4-[(cyclopentylsulfonyl)amino]phenyl} propanamide;
(2R)-2-(4-{[(trifluoromethyl)sulfonyl]amino}phenyl) propanamide;
(2R)-2-{4-[(isopropylsulfonyl]amino} phenyl)-N-methylpropanamide;
(2R)-N-[( 1 S)-2-amino-1-methyl-2-oxoethyl]-2-(4-[(isopropylsulfonyl]amino} phenyl) propanamide;
(2R)-2-{4-[(isopropylsulfonyl]amino} phenyl)-N-[4-(trifluoromethyl)-1,3-thiazol-2-yl]propanamide;
(2R)-2-{4-{[(2-chlorophenyl)sulfonyl]amino} phenyl)-N-[4-(trifluoromethyl)-1,3-thiazol-2-yl]propanamide;
(2R)-2-{4-{[(2-chlorophenyl)sulfonyl]amino} phenyl)-N-[2-(2-hydroxyethoxy)ethyl]propanamide;
(2R)-2-{4-{[(2-chlorophenyl)sulfonyl]amino} phenyl)-N-cyclopropylpropanamide.

4. Compounds according to claim 3 which are:
(2R)-2-{4-[(isopropylsulfonyl]amino} phenyl)propanamide and its sodium salt.

5. A method for the treatment of diseases that involve CXCL1 induced human PMNs chemotaxis selected from the group consisting of chronic obstructive pulmonary disease (COPD) and obliterans syndrome (BOS) comprising administering to a subject in need thereof an effective amount of a compound of claim 1.

6. Pharmaceutical compositions comprising a compound according to claim 1 in admixture with a suitable carrier thereof.

7. Process for the preparation of compounds of formula (I) according to claim 1 comprising the reaction of compound of formula (II),

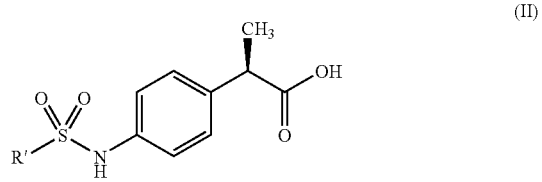

wherein R' has the same meaning as defined in claim 1, with an amine of formula NHR,
wherein R has the same meaning as defined in claim 1.

8. Process for the preparation of compounds of formula (I) according to claim 1 comprising the reaction of (2R)-2-(4-Aminophenyl)propanamide with a sulfonyl chlorides of formula R' SO₂Cl, wherein R' has the same meaning as defined in claim 1.

* * * * *